United States Patent [19]

Kiser et al.

[11] Patent Number: 5,306,623
[45] Date of Patent: Apr. 26, 1994

[54] VISUAL BLOOD GLUCOSE CONCENTRATION TEST STRIP

[75] Inventors: Ernest J. Kiser, Los Altos; Edward G. Rice, Palo Alto; Michael F. Tomasco, Mountain View, all of Calif.

[73] Assignee: Lifescan, Inc., Mountain View, Calif.

[21] Appl. No.: 736,537

[22] Filed: Jul. 26, 1991

Related U.S. Application Data

[63] Continuation-in-part of Ser. No. 578,364, Sep. 6, 1990, abandoned, which is a continuation-in-part of Ser. No. 399,055, Aug. 28, 1989, abandoned.

[51] Int. Cl.[5] ............... C12Q 1/54; C12Q 1/26; C12Q 1/28; G01N 21/00
[52] U.S. Cl. ............................. 435/14; 435/4; 435/25; 435/28; 422/57; 436/177
[58] Field of Search ............ 422/56, 57, 101; 435/4, 435/14, 25, 28; 436/177

[56] References Cited

U.S. PATENT DOCUMENTS

| | | | |
|---|---|---|---|
| 3,992,158 | 11/1976 | Przybylowicz | 23/253 |
| 3,995,019 | 11/1976 | Jerome | 424/1.5 |
| 4,018,883 | 4/1977 | Parslow | 424/1 |
| 4,654,310 | 3/1987 | Ly | 436/164 |
| 4,734,360 | 3/1988 | Phillips | 435/25 |
| 4,748,114 | 5/1988 | Kallies et al. | 435/14 |
| 4,824,639 | 4/1989 | Hildenbrand | 422/56 |
| 4,994,238 | 2/1991 | Deflora et al. | 422/56 |

Primary Examiner—Michael G. Wityshyn
Assistant Examiner—Ralph Gitomer

[57] ABSTRACT

A separation matrix impregnated with a separating agent separates red blood cells or hemoglobin from whole blood. Upon separation, an impregnated test reagent reacts with the separated substantially clear component fluid to form a colored product which enables a visual or meter test for analyte levels in whole blood. Such a test is appropriate for, among other things measuring glucose, cholesterol, or alcohol levels in whole blood samples. A visual meter is disclosed which allows sample to be applied to one side of the strip, and reading takes place on the opposite side, after separation of red blood cells and reaction to test reagent. Also, a useful test strip format is disclosed.

7 Claims, 3 Drawing Sheets

VISUAL BLOOD GLUCOSE CONCENTRATION TEST STRIP

This application is a continuation-in-part of Ser. No. 578,364, filed Sep. 6, 1990, entitled "VISUAL BLOOD GLUCOSE CONCENTRATION TEST STRIP", now abandoned, which is a continuation-in-part of Ser. No. 399,055, filed Aug. 28, 1989, entitled, "Blood Separation and Analyte Detection Techniques, now abandoned."

FIELD OF THE INVENTION

The present invention relates to a technique which allows the user to comparatively determine analyte concentration levels in whole blood. More particularly, the present invention relates to a comparative reagent strip which allows the user to determine concentration levels of analytes in whole blood. Most specifically, the present invention relates to a comparative reagent strip which separates whole blood into component red blood cells and a clear fluid and from which is determined analyte concentration levels in the fluid, which correlate to concentration levels of the analyte in the sample. These concentration levels are determined through means of a visual comparison test or various instrumental metering means.

BACKGROUND OF THE INVENTION

Numerous simple visual test devices have been developed for the analysis of body fluids in order to determine component analyte concentrations. These tests include such devices as means for detecting, for example, glucose or other sugars, cholesterol, proteins, ketones, uric acid, phenylalanine, or enzymes in either blood or urine. Yet, it has been particularly difficult to perform visual measurements of these constituents in whole blood. This difficulty lies in the problems associated with visual interference caused by the presence of red blood cells in whole blood. The deep red coloration of red blood cells or free hemoglobin seriously interferes with such whole blood visual analyte concentration analysis.

Means have been proposed for separating and removing highly colored red cells and hemoglobin from whole blood prior to analysis. Some of the simpler methods involve the use of a carrier member impregnated with a test reagent composition and coated with a semipermeable membrane which effectively acts as a means for screening out cells or large molecules such as hemoglobin. This semipermeable membrane permits the passage of smaller molecules or ions in the solution. A substantially clear fluid containing the constituent diffuses into the test reagent in the carrier to cause a chromogenic reaction with the reagent.

Other methods have included taking whole blood samples and placing such samples on a bicomponent reagent strip. After a predetermined time period, the blood sample is blotted to remove excess blood from the top of the strip. At that point, constituents of the whole blood sample migrate onto the strip, and then react with reagent molecules embedded in the reagent strip, and a visual comparison of the resultant color of the reacted blood is made to a chart or standard.

These methods are cumbersome and generally laborious and require at least one extra manipulative step, such as wiping, blotting or rinsing with water. This amounts to considerable loss in time and more importantly, accuracy and efficiency. Moreover, the filtering membrane screens out larger molecules in solution, which precludes these molecules from reaching the test reagent. This sometimes renders these methods inoperative for particularly needed determinations, such as determination of glucose concentration levels. These methods are also technique-dependent and difficult for untrained operators to perform in a reproducible fashion.

Additional methods provide for the drawing of a whole blood sample, then allowing the blood to clot. Once clotted, the blood is centrifuged to separate cellular components from fluid components. These methods require equipment generally found only in specialized settings and typically are more labor intensive than the previously mentioned methods.

Other test systems may comprise a single matrix which contains both a separating component and a test reagent impregnated in the reagent in such a way that the whole blood first contacts the separating component to form a substantially colorless fluid which then contacts the test reagent. In employing such a single matrix test system the separating component and the test reagent must be stable and reactive in each other's presence. The matrix must be designed so that the analyte contained in the whole blood sample reaches the area of the matrix where the response is read by a meter, in a state that is substantially free of any blood coloration. In such an embodiment, a porous support is first coated or impregnated with the test reagent and subsequently the surface of the matrix is coated or impregnated with the separating component. In such a test matrix device, the whole blood contacts first the separating component and the test response is observed in an area not initially in contact with the blood and to which the substantially colorless fluid has migrated.

Examples of such single matrix test strips included separating components which have been found to be, among other things, water-soluble salts, amino acids and carbohydrates such as mannitol. Some of these chemicals cause hemolysis, which is the release of cellular constituents, including hemoglobin. The salts found effective as separating components are non-volatile and do not decompose to any extent under the conditions of preparing and utilizing the test device. The salts have been defined as having solubility in distilled water of at least about 1 gram per liter at 20° C.

Yet, in many instances, fluid containing red blood cells or hemoglobin continues to seep through the matrix despite the presence of the separating component causing the test to mix reagent with colored blood components. When this occurs, accuracy is compromised, and visual comparison is difficult.

It is thus an object of the present invention to provide a unitary test device, wherein during one step the user can apply an unmeasured sample of whole blood and determine the concentration level of an analyte in the whole blood sample.

It is therefore another object of the present invention to provide a unitary test device wherein the test device, whether single or multi-layer, contains separating means as well as test reagent.

It is a further object of the present invention to form a test device consisting of a single matrix wherein whole blood samples can be applied to one side of the matrix and a visual comparison of the analyte concentration level can be made at the opposite side of the test strip. Alternatively, in a longitudinal transport device, such readings can be made on a second portion of the test strip after wicking away from the first portion of the matrix, where the solution sample has been applied.

It is yet a further object of the present invention to determine glucose levels in whole blood samples where a wholly unmeasured sample of whole blood is applied to a single side of a reagent strip. The separating component and test reagent are coated on or trapped within the reagent strip. The test strip then effectively and simultaneously separates the blood into constituent clear fluid and red blood cells and reacts with the glucose in the clear fluid in a manner enabling one to determine, visually, glucose concentration levels of the wholly unmeasured whole blood sample.

It is finally an object of the present invention to provide a test device such that whole blood is analyzed in a single manipulative step for selected molecular constituents such as glucose by a combination of separation means and detection means.

SUMMARY OF THE INVENTION

These and other objects of the present invention are accomplished in a single membrane test strip matrix which is attached to a support member. This test strip is treated with both a separating component and a testing reagent, both of which are impregnated or embedded into the test strip. Both the separating component and test reagent may be found throughout the entire test strip matrix or each of these components may be found predominately on one respective side of the matrix.

In the method of the present invention, whole blood is applied to one side of the matrix. As the whole blood passes through the matrix, separation and reaction occur. Ultimately, the whole blood is separated into red blood cells and a substantially colorless fluid. Because the matrix is configured with such a thickness to cause the red blood cells to become separated within a first portion of the strip of the matrix, a second or lower portion of the matrix contains substantially clear component fluid. Analytes in the component fluid react with the test reagent without potential interference from the colored components in whole blood.

The test reagent is, of course, configured to accurately determine the analyte concentration levels, generally by a visual comparison means. Therefore, the resulting observable reaction on the test side of the matrix will be a product of the test reagent reacting with the analyte in the separated clear fluid component. This enables visual or instrumental determination of analyte concentration levels, in direct proportion to the concentration of the analyte in the whole blood sample.

In an alternate embodiment of the present invention, whole blood is placed on a sampling surface comprising a disc of porous material able to absorb the sample. The disc serves as a transport mechanism for the sample. The disc is then contacted with a matrix treated with both separating reagent and test reagent. The blood then separates and reacts. A final visual comparison is then made on the test side of the matrix, away from the porous disc.

In addition, the present invention may be configured so that a separating membrane portion and reagent membrane portion are incorporated within the same test strip matrix. The previously described separation techniques are applied to the whole blood sample. After separation, the same analyte concentration level reaction takes place between the separated sample and the testing reagents impregnated in the reagent membrane portion.

Alternately, the device may be configured so that some or all of the reaction between the analyte contained in the sample and the test reagent occurs before blood separation. This embodiment signifies that the actual ordering of separation and reaction is unimportant, as long as the end result is a test surface for reading the results where a color change occurs, which is both related to the concentration of the analyte in the sample and unobscured by significant visual interference from the red coloration of the whole blood sample.

In yet another additional embodiment, the test matrix strip may be configured to be a tri-folded panel, in which the blood enters through capillarity. The blood first fills a capillary area, separates into red cells and clear component. The analyte reacts with the test reagent when the test reagent contacts clear fluid component, and a color change occurs on an opposite side of the strip, apart from the location of application. Quantification of the color change is made by either optical meter methods or visual comparison.

The present invention will be more accurately understood in conjunction with the following detailed description of the invention as well as the present detailed description of the drawings.

DETAILED DESCRIPTION OF THE DRAWINGS

DETAILED DESCRIPTION OF THE INVENTION

The subject invention provides an improved rapid, simple methodology implying a reliable and easy to operate apparatus for determination of analytes such as glucose, particularly involving a substrate, which results in a change in color in order to determine analyte concentration levels in whole blood. The method involves applying to a porous matrix a small volume of whole blood, sufficient to saturate the matrix. The matrix may be either one single layer uniformly embedded with reagent and capable of separating whole blood, or it may be a unitary composition matrix comprising a separation layer and testing reagent layer. Bound to or contained in the matrix are one or more components of a signal producing system, which produce a change in the color of the matrix when combined with analytes in blood. The liquid sample penetrates the matrix and an observation of color change is made on the opposite side of the matrix from where the sample is placed. The color change can be read visually, due to the separation of whole blood into colored constituent components and a clear fluid, such that there is a reaction of analyte contained in the clear component with a testing reagent impregnated in the matrix.

For measurements of analytes in blood, particularly glucose measurements, whole blood is typically used as the assay sample. The matrix will be impregnated with both a separating component and a testing reaction agent. The testing reaction agent alters a light absorbing product which changes either in color or intensity, dependent upon concentration of the analyte in the whole blood sample. The time span within which the blood separates and reacts typically varies from about 15 seconds to about 5 minutes.

Figure 1:
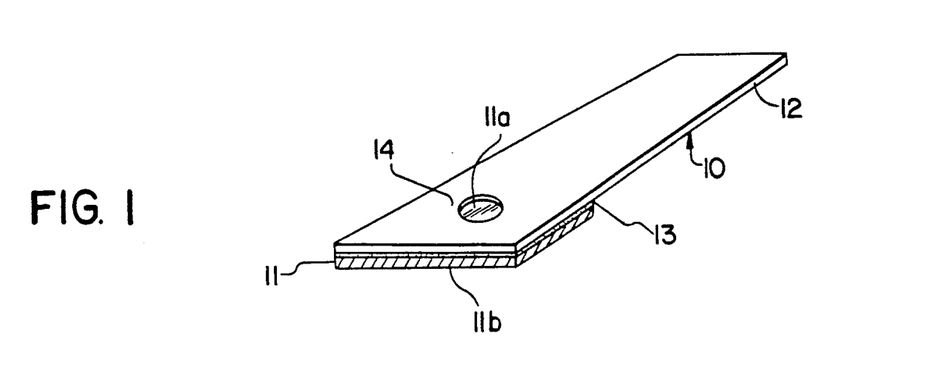
FIG. 1 is a perspective view of a preferred embodiment of a test strip of the present invention.

A first embodiment of the present invention comprises the test strip 10 containing a reagent element 11, as seen in FIG. 1. This reagent element 11 is comprised of an inert porous matrix and embedded with the component or components of a signal producing system, which is capable of reaction with an analyte in blood to produce a color variable reaction product on the side of the porous matrix away from where sample has been applied. The signal producing system allows flow of liquid through the matrix. In order to assist in reading the color-produced scheme, it is preferred that the matrix have at least one side which is substantially smooth and flat. Typically the matrix will be formed into a thin sheet with at least one smooth, flat side.

In use, the liquid or whole blood sample being analyzed is applied to one side of the matrix on test strip 10 whereby the desired analyte passes through the reagent element 11 by means of capillary action, wicking, gravity flow and/or diffusion. The components of the signal producing testing reagent system present in the reagent matrix element 11 will react to vary a light absorbing reaction product, whose color will be dependent upon the analyte concentration in the liquid sample.

The first component of the reagent element 11 is the matrix itself. The matrix will be a porous material to which separating components or testing reagents may be covalently or noncovalently bound or impregnated. The matrix will allow for the flow of an aqueous medium through the matrix. The matrix 11 will also retard passage of whole blood cells through the matrix without substantial hemolysis and without significantly adversely affecting the identity or concentration of the analyte in the blood sample, especially in the resultant clear component fluid. Importantly, the matrix will be easy to manufacture reproducibly; this will result in proper amounts of testing reagent being contained in the matrix.

The matrix 11 will be of sufficient thickness, preferably 50 to 3000 microns, to permit the formation of a colored reaction product on the test side 11b of the matrix, that is the side opposite that side 11a where the sample is applied, so that constituents of the essentially clear fluid react with the test reagent embedded in the matrix 11. The matrix also should not deform substantially upon wetting so as not to interfere with subsequent quantitation. The matrix 11 thus substantially retains its original size and flatness.

As exemplary of matrix surfaces are porous polyamides, especially polyamide matrices having a porosity of between 0.1 and 150 microns. Especially useful are matrices which are coated or impregnanted with polyethylene glycol, polystyrene sulfonic acid or polyvinyl sulfonic acid at a pH between 4.0 and 8.0. However, it has been observed that sufficiently opaque thicknesses of paper will also be effective as a matrix, as well as woven or non-woven Polyesters and polyamides and other absorptive surfaces, such as nitrocellulose.

One manner of preparing the porous material which forms the matrix is to cast the hydrophilic polymer onto a core of nonwoven fibers. The core fibers can be any fibrous material with requisite integrity and strength, such as the aforementioned polyesters or polyamides. The testing reagent and the components that will form the separating and reacting material is present within the pores of the matrix but does not block liquid flow through the matrix. Thus, the separated clear constituent fluid can pass through the pores of the matrix, while red blood cells and hemoglobin are retarded at or near the matrix surface near where sample has been applied.

It has been found especially useful to use as a matrix a polysulfone membrane having a cell porosity of between 0.1 and 150 microns. Such a polysulfone membrane, when treated with appropriate separating components and testing reagents, adequately forms a single layer matrix which rapidly separates a substantially clear fluid from whole blood. Consequently, the color produced by the reaction of the analyte of interest with the signal producing testing reagents can be observed in an area not initially contacted by the blood, without substantial interference from the highly colored components of whole blood.

A matrix of less than about 3000 microns thickness is usually employed, with about 100 microns to about 1000 microns being preferred. Typically, the matrix will be attached to a holder 12 in order to give it physical form and rigidity, although this is not essential. FIG. 1 shows an embodiment of the invention in which a thin hydrophilic reagent element comprising matrix 11 is positioned at one end of a plastic holder 12 by means of an adhesive 13 which directly and firmly attaches the matrix 11 to the holder 12, which results in holder 12 acting as a handle. A hole 14 is present in the plastic holder 12 in the area to which reagent element 11 is attached so that sample can be applied through hole 14 to one side 11a of the reagent element 11 and reaction product observed on the opposite side 11b of the matrix 11.

A liquid sample to be tested is applied to reagent element 11. Generally, with blood being exemplary of a sample being tested, the matrix will be on the order of about 10 mm sq. to about 100 mm sq. in surface area, especially 10 mm sq. to 50 mm sq. in area, which normally a volume of 5 to 20 microliters of sample will more than saturated. As can be seen in FIG. 1, the plastic holder or support 12 holds reagent element or matrix 11 so that the sample can be applied to one side 11a of the reagent element 11, 10 while color can be observed on the opposite side 11b of the reagent element 11.

Figure 3:
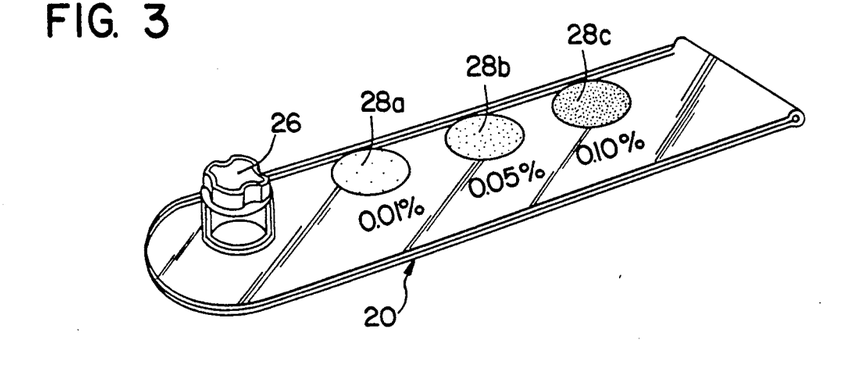
FIG. 3 is a perspective view of a second alternate preferred embodiment of a test strip of the present invention in a closed position.
Figure 4:
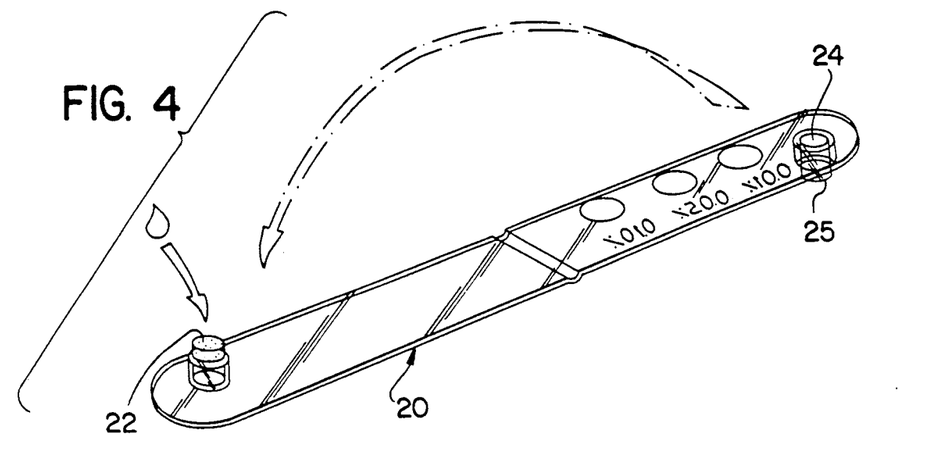
FIG. 4 is a perspective view of a second alternate embodiment of the present invention in an open position.
Figure 5:
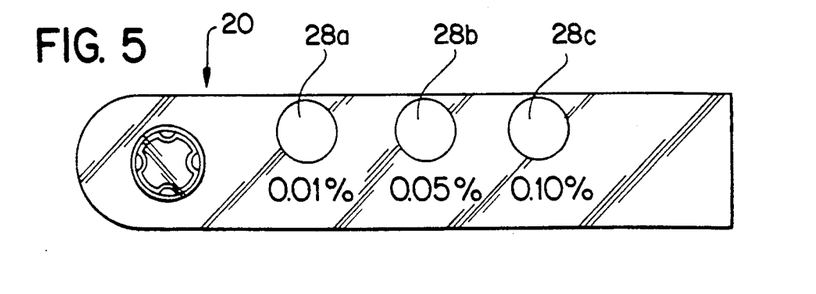
FIG. 5 is a top view of a second alternate preferred embodiment of the present invention in the closed position.

FIGS. 3, 4 and 5 which show a system in which reagent is applied to a porous disc 22 on one side of a folding strip 20. This folding strip has a well 24 containing matrix 25 opposite disc 22. Disc 22 fits into well 24 when strip 20 is folded. As seen in FIGS. 3 and 4, the strip 20 is folded so that the matrix 25, which is similar to the matrix 11 of FIG. 1 in both function and design, can react with a whole blood sample placed on disc 22.

As seen in FIG. 5, what is observed will be the reaction product through comparator 26 which can be visually compared to color patches 28a, 28b, 28c placed like a scale alongside the pad. The patches have colors typical of those formed by the reaction product.

The matrices 11, 25 embodied in FIGS. 1, 3, 4 and 5 may be attached to the support by any convenient means, e.g. a holder, clamp or adhesives; however, the preferred method is bonding. The bonding can be done with any noninterfering adhesive, by a thermal method in which the backing surface is melted enough to entrap some of the material used for the matrix 11, 25, or by microwave or ultrasonic bonding methods which likewise fuse the hydrophilic sample pads which form the matrix 11, 25 to the backing. It is important that the bonding be such as to not itself interfere substantially with either reaction between reagent element 11, 25 and whole blood sample or the separation process acomplished in each matrix 11, 25. For example, an adhesive 13 can be applied to the backing of plastic holder or strip 12, followed by punching hole 14 into the strip 12 and then applying reagent pad 11 to the adhesive 13 in the vicinity of hole 14 so that the peripheral portion of the reagent pad element 11 attaches to plastic strip 12.

Turning to the components embedded into these matrices, among other things, the separating component should be capable of producing a relatively clear colorless fluid from whole blood by sequestering the red cells in the matrix 11. Separating components must be contained within the matrix 11 in cooperation with testing or reaction reagents, as will later be explained. In varying degrees, water soluble salts effect such separation. Among salts operable as a separating components in these embodiments of the present test device are citrates, formates and sulfates as well as certain acids such as amino acids, citric acid, phytic acid and malic acid.

In addition to such salts or acids, polymeric separating components have also been found effective, such as polyethylene glycol, polystyrene sulfonic acid, polyvinyl sulfonic acid, polyacrylic acid, and polyvinyl alcohol impregnated or embedded in and used in conjunction with matrices or membranes such as the Pall BioSupport TM membrane. It has been found that it is necessary to treat at least a portion of the matrix so that it is embedded with such a separating agent.

Signal producing systems which comprise testing reagents typically employed in light reflectance measurements can also be used in conjunction with these matrices embedded with separating components to perform visual comparison readings. As previously described, the separating components embedded in the matrix cause red blood cells to be separated from whole blood, thereby producing a substantially clear constituent. At that point, a testing reagent forming a signal producing system such as those embodied in the One-Touch TM test strip described in U.S. Pat. No. 4,935,346, and incorporated herein by reference, may be employed, which cause the analyte in the sample to produce compounds characteristically visually observable on the opposite side of a matrix bound to the reagent strip. Alternately, the strip may be optically tested in conjunction with a meter, such as that employed using the previously referenced One-Touch TM system.

The preferred analysis method is to apply an unmeasured drop of whole blood on one side of the matrix. As the whole blood sample moves into or across the matrix, it encounters the separating component embedded into the matrix. At that point, a substantially clear colorless component is separated from the red blood cells and the analyte in the component reacts with the embedded testing reacting agent in order to produce a visually observable color change.

Figure 2A:
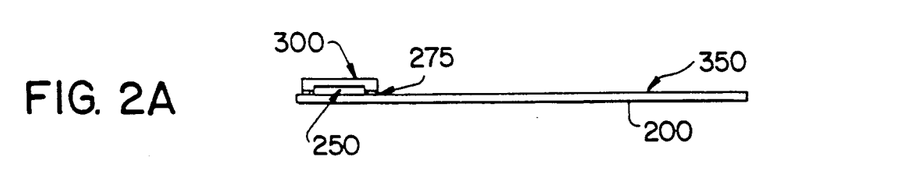
FIGS. 2a, 2b and 2c are top, bottom and side views of an alternate preferred embodiment of the present invention.
Figure 2B:
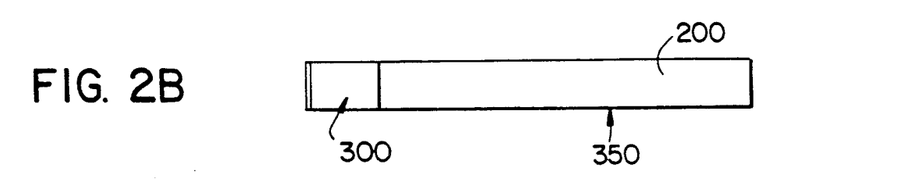
Figure 2C:
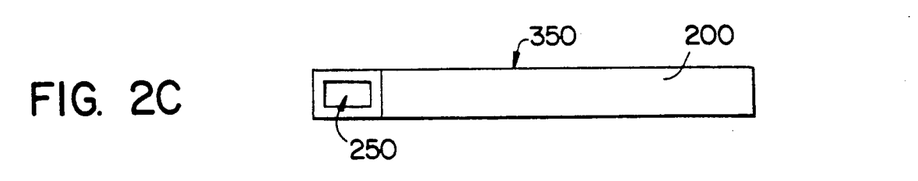

An additional preferred embodiment of this type of system is seen in FIGS. 2a, 2b and 2c. Here, there is a test strip 350 comprising clear plastic support 200, which is adhesively connected to a coated reaction or reagent matrix 250 and a coated separation matrix 300. Each of these components of the test strip 350 will be explained in sequence.

The first component is the coated separation matrix 300. This separation matrix will generally be between 50 and 3000 microns in thickness. The matrix 300 is formed from among the families of polyesters, polyamides, polyolefins or cellulosics. Among the viable candidates are those polyester membranes made by Porex Corp. Among the available materials useable to coat or impregnate into the separation matrix 300 are polyvinyl sulfonic acid, (PVSA), polyethylene glycol (PEG), polystyrene sulfonic acid (PSSA), hydroxypropyl cellulose (commercially available as Klucel TM ), polyvinyl alcohol (PVA), polyvinylpyrrolidone (PVP), polyacrylic acid (PAA) or any such equivalent materials for separating whole blood into red blood cells and a clear constituent fluid, combined with particulate additives such as silica or clay.

The separation matrix layer 300 is of a uniform composition with reagent matrix 250. Separation matrix layer 300 is combined with a testing reagent layer containing reagent matrix 250 placed under or within separation matrix 300. The reagent coated matrix 250 may be chosen from among polyamides, polysulfones, polyesters, polyolefins or cellulosics and bound to support 200 by adhesive layer 275. Reaction matrix 250 is embedded with a testing reagent indicator solution. All indicator solutions described are provided in a 0.1M, 5.0 pH citrate buffer containing 1% Klucel TM -EF with testing reagent enzymes comprising glucose oxidase at 6 mg/ml and horseradish peroxidase at 2 mg/ml.

The indicator solutions useful as reagents for coating impregnating in the reaction matrix 250 may be chosen from among (a) 3-methyl-2-benzothiazolinone hydrazone hydrochloride (MBTH) combined with 3,3-dimethylaminobenzoic acid (DMAB); (b) MBTH combined with 3,5-dichloro-2-hydroxybenzene-sulfonic acid (DCHBS); (c) 4-aminoantipyrene(4-AAP) (at 4 mg/ml) and 5-oxo-1-(p-sulfophenyl)-2-pyrazoline-3-carboxylic acid (OPSP); (d) 4-AAP (at 4 mg/ml) and N-(m-tolyl)-diethanolamine (NDA); (e) 2,2'-azino-di (3-ethylbenzthiazoline) sulfonic acid (ABTS); or (f) 4AAP (at 4 mg/ml) and 4-methoxynaphthol; (g) pyrogallol red (PGR); (h) bromopyrogallol red (BPR); or (i) acid green 25 (AG).

Further regarding the indicator solutions described above, the MBTH concentrations are found most effective at 2 mg/ml. In addition, when MBTH is combined with DMAB or DCHBS, each of these other components are used within the matrix at concentrations of 2 mg/ml. The 4-AAP/OPSP concentration is generally used 1 mg/ml. On the other hand, NDA concentrations can be used most effectively at 0.2 mg/ml. As well, the ABTS combination is most useful at 5 mg/ml. Finally, PGR, BPR, and AG are effective within a range of about 0.1 to 10 mg/ml, with about 1 mg/ml being optimum.

In addition, these indicator solutions can be combined with substances such as polyethylene glycol, Polyquart TM, or Klucel TM in order to be better bound to the reaction matrix 250.

It has been found that the polymer impregnated separation matrix 300 may include a component which acts as a surface tension modifier capable of releasing analyte from the separated component fluid. The separation matrix 300 is then be combined with a testing reagent embedded reaction matrix 250. It has been found that tetraethyleneglycol dimethyl ether is quite useful as an tension modifier or "analyte releaser" in performance of the present invention.

In addition, the separation matrix 300 has been found effective when an amount of testing reagent is impregnated within the separation matrix 300 itself. Of course, additional testing reagents are then impregnated within the reaction matrix 250, all within the same test strip 350. It has been found quite useful to provide a separation matrix 300 comprised of polyethylene embedded with a polyethylene glycol separation component and including within the separation matrix 300 glucose oxidase and an appropriate citrate buffer. As well, impregnated in the reaction matrix 250 it has been found useful to provide any of the previously listed indicator solutions combined with testing reagent comprising horseradish peroxidase.

Certain components embedded in separation matrix 300 have been found quite useful to adequately separate whole blood samples. Any of the above matrix materials can be used wherein the separation matrix component combinations are chosen from the following examples:

1. 35% weight per volume (W/V) PEG 3500 in methylene chloride as a component, used on fine polyethylene as a matrix 2. 10% (W/V) PVSA and 1% (W/W) Bentonite in water at pH 5.0 (component) on fine polyethylene (matrix)

3. 13% (W/V) Monostearate of PEG in methylene chloride (component) on fine polyethylene (matrix)

4. 20% (W/V) PEG 1000 and 2% (W/W) Bentonite in methylene chloride (component) on nonwoven rayon (matrix)

5. 4% (W/V) Tetraethylene glycol dimethyl ether and 30% (W/V) PEG 1000 in methylene chloride (component) on nonwoven polyester (matrix)

6. 15% (W/V) PVSA and 0.2% (W/V) PVA 10000 in water at pH 4.5 (component) on a polyethylene or a woven nylon membrane (matrix)

7. 7% (W/V) PVSA in water at pH 4.5 (component) on the commercially available Pall L/4 polyester (matrix)

The following preferred reagent matrixes 250 using certain dye indicator solutions have been found to be useful:

1. One Touch TM polyamide reagent membrane, made by LifeScan, Inc.

2. MBTH plus DCHBS on a polyamide membrane, 3. 4-AAP plus NDA on a polyamide membrane, 4. One Touch TM polyamide reagent on a polysulfone membrane Finally, it should be noted that the plastic strip 200 should be between 50–1000 microns in thickness and be comprised of a transparent, clear plastic. This plastic strip 200 provides support for the entire assembly, and provides the base for the testing apparatus. As well, reading takes place through the underside of strip 200, and observing reagent matrix 250.

Thus, the separation matrix 300 is placed above the reaction matrix 250 and is adhered as at 275 to the clear plastic strip 200. When a whole blood sample is placed upon the separation matrix 300 layer, the blood sample is separated in the separation matrix 300 and a clear constituent fluid then enters the reaction matrix 250. In the reaction matrix 250, the analyte in the separated fluid reacts with testing reagent, which is coated or embedded in the reaction matrix 250, and a color change is visible through the clear plastic strip 200. At the surface of the clear plastic strip 200 a comparison can be made with a standardized color chart to determine analyte, in this particular case, glucose. Alternately, an opaque plastic with a punched window such as in FIG. 1 can be used instead of a clear plastic.

Yet a further embodiment of the visual glucose test strip format consists of a reagent matrix to which varying inhibitor/indicator concentrations are applied in segments or stripes from either an aqueous solution or a thickened organic aqueous solution. Alternately, the various components of a signal producing system as well as the varying reactive concentrations of a dye inhibitor inhibitor/dye indicator solution are applied simultaneously to the porous matrix in segments, leaving nonreactive zones between each segment. Blood separation can be accomplished either by using a separate blood separating layer matrix in conjunction with the banded reagent layer matrix, or by creating a single layer matrix which contains both signal production reagents and blood separation components, as previously described. Such a particular configuration can be better understood when observed in conjunction with FIGS. 6, 7a, 7b and 7c.

A particularly useful example of the above mentioned embodiment of the invention is a format consisting of a reagent or test membrane or matrix embedded with the following components: reagent enzymes, buffer, separation component agents and/or hematocrit adjusting agents, chelator, a dye indicator (testing reaction agent) and, optionally, a stabilizer. After coating the membrane with the described components, varying inhibitor and/or indicator concentrations are applied in segments or strips from an aqueous solution or an aqueous/alcohol/thickener solution. Printing may also be used to apply the inhibitor and/or dye. Table 1 describes the individual chemicals or materials used in such an example visual test strip:

TABLE 1

| Components for Glucose Measurement Strip | |
|---|---|
| Enzymes | Glucose oxidase |
| | Horseradish peroxidase |
| Blood Separation/ Hematocrit Adjustor/ Stabilizer | Chitosan (Amino sugar) |
| | Hydroxypropyl cellulose [Klucel TM] |
| | Hydroxyethyl cellulose [Natrasol TM] |
| | Methyl Vinyl Ether and Maleic Anhydride copolymer [Gantrez TM] |
| Component | Polyethylene Glycol |
| | Polyvinyl Sulfonic Acid |
| | Polyacrylic Polymers [Carbopol TM] |
| | Polyethylene Glycol-15 tallowamine [Polyquart TM] |
| | Polyethyleneimine |
| | Polypropylene Glycol |
| | Polyacrylic Acid Polymer [Carbopol TM] |
| | Polystyrene Sulfonic Acid |
| Buffer | 2-(N-Morpholine)-ethane acid [MES] |
| | Fumaric Acid |
| | Malic acid |
| | Citric acid |
| | Aconitic Acid |
| Chelator | Ethylene Diamine Tetraacetic Acid (EDTA) |
| Dye | Alizarin Cyanin Green [Acid Green 25] |

TABLE 1-continued

| Components for Glucose Measurement Strip | |
|---|---|
| Indicator (Testing Reagent) (Applied in Varying Concentration Levels) | 5',5"-Dibromopyrogallol-sulfonephthalein [Bromopyrogallol Red] Anazolene Sodium [Acid Blue 92] Pyrogallolsulphonphthalein [Pyrogallol Red] 2,2' Azino-di-[3]ethylbenzthiazoline sulfonate (ABTS) |
| Inhibitor | 2,3,4-trihydroxybenzoic acid Propyl gallate Ascorbic acid Isoascorbic acid 3,4 dihydroxy cinnamic acid 3,4 dihydroxy benzaldehyde Gallic acid 5,6-diaminouracil |
| Testing Membrane | Anisotropic hydrophilic polysulfone Anisotropic hydrophobic polysulfone Polyester membrane Cellulose acetate membrane |
| Support | Mylar TM Coated paper Nylon |

The stabilizer is able to maintain the "stripes" or segments in their proper place on the test strip. These stabilizers, in effect, keep the indicator (and/or inhibitor, as later explained) from migrating on the test strip matrix so that proper concentration ratios of active components are maintained between strips. "Indicator" refers to the component of the signal generating system which changes color in the course of the reaction. Inhibitors create the cutoff levels of "stripes" on each strip so that concentration level may be determined from the number of stripes that are activated. All indicators except ABTS are subtractive. That is, color is removed from each band as the peroxide reaction product of indicator and the glucose in the sample exhausts or overcomes the inhibitor in that band. For instance, a sharply colored band, such as blue, turns white when all the inhibitors in a stripe or band is overcome. The point at which the color of the band changes can be controlled by adjusting inhibitor and indicator levels either singly or in combination.

Importantly, an anisotropic membrane for use with the test strip has proved quite useful. This membrane, generally about 0.005" thick, has a perceived opacity to the sample resting above it, due to the increased density of pores encountered as the sample penetrates the membrane. When blood separation is effected, most of the colored components in whole blood cannot be seen from the underside of the membrane because a sufficiently thick opaque zone exists between these components and the optical viewing surface. The glucose contained clear component fluid, however, can penetrate to the bottom of the membrane. In addition, the anisotropic nature of the membrane permits rapid flow rates through the membrane. A combination of these features allows the membrane to be a highly effective single layer matrix containing both reaction testing reagents and separation components. A color change relating to the concentration of an analyte in whole blood can be read visually on the underside of the membrane substantially free from interference caused by the highly colored blood components separated above it in the anisotropic membrane.

Specifically, it has been found that certain anisotropic membranes have proven quite useful in accomplishing the present invention. The device is constructed so that the anisotropic membrane is positioned with a wider pore size laminated to a support layer through use of a discontinous adhesive. After blood is placed on a porous support membrane, the blood sample is able to progress from the porous support through the larger pore sections and ultimately toward the test side of the membrane. This system allows colored reaction product to be readily observed.

Some advantages realized by this format are derived from the use of a porous support which simultaneously serves as membrane holder and fluid conductor to allow the manufacture of very inexpensive test strips. Second, an extremely fast reaction test device can be constructed. For instance, it is found that glucose devices will have reaction speeds within a ten to 30 second readout range. Third, importantly, it has been found that this format is conducive to maintaining a stable endpoint, so that readout is maintained for a great deal of time after the test has been accomplished. Ideally, it would be desirable to have the color of the readout be maintained even when the membrane which forms this strip is dry.

Useful concentration levels of the various components impregnated in the test strip matrix depend on the specific components chosen and their interaction with one another. For example, using PGR as an indicator, PEI is a far more effective stabilizer than Polyquart TM and can consequently be used at a lower concentration in the formulation. With this in mind, some useful component levels are as follows: 0.1 to 10 mg/ml indicator, preferably about 1 mg/ml; 0.05 to 1 M buffer, preferably about 0.2 M; 2 to 20 mg/ml glucose oxidase, preferably about 7 mg/ml; 1 to 19 mg/ml peroxidase, preferably about 3 mg/ml; 0.05% to 5% stabilizer, perferably about 1%; and 0.5% to 20% hematocrit adjusters, perferably about 4%. The inhibitor application method has a strong influence on inhibitor effectiveness, but levels between 0 and 40 mg/ml saturation levels coated from an aqueous solution are generally appropriate.

Figure 6:
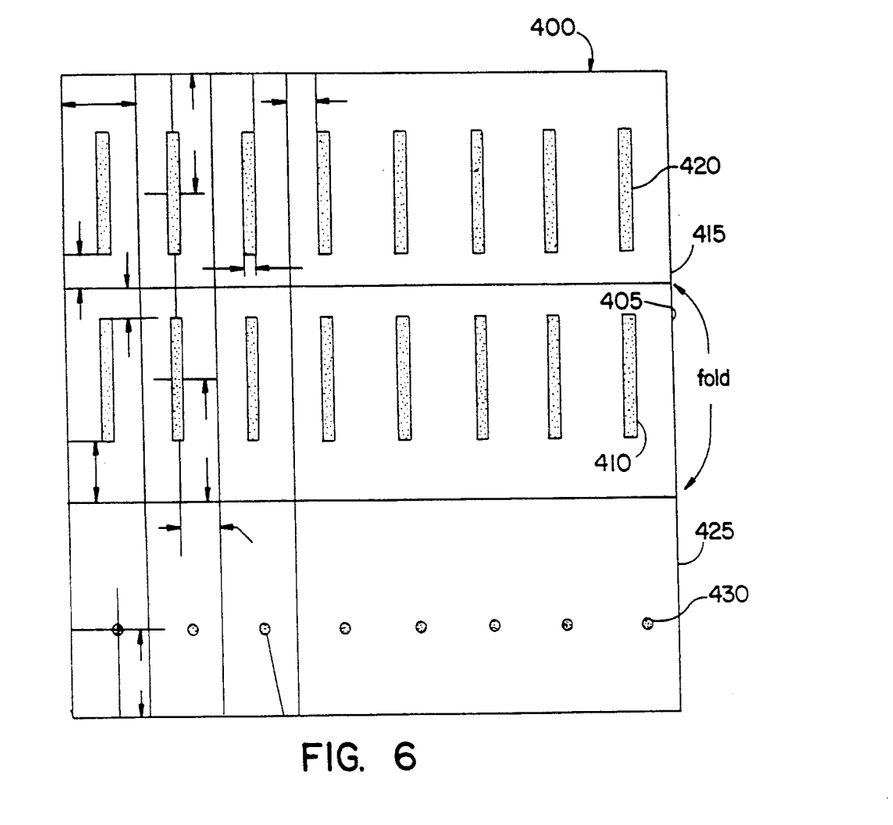
FIG. 6 is a plan view of a further alternate embodiment of a strip template of the invention.

Turning to the drawings, FIG. 6 shows an assembly format for multiple strips. A template 400 has mounted on it a membrane like those used in FIGS. 1, 3 and 2a (not shown) which straddles the center layer 405 containing slits 410. Each prepared membrane has a reagent segment which approximately matches the slits 410. These open slits are roughly ⅛" wide and about 1" long. Upper section 415 is folded over the membrane so that slits 420 are matched over slits 410. These slits 420 describe the same opening as slits 410 and provide capillary void useful for application of sample. Finally, lower layer 425 is folded over upper layer 415 so that the holes 430 are centered over slits 420. Each such hole 430 is about ⅛" diameter. Then each trifolded segment is cut between slits 410 to create a member of separate reagent strips 440, as better seen in FIGS. 7a, 7b and 7c.

Figure 7A:
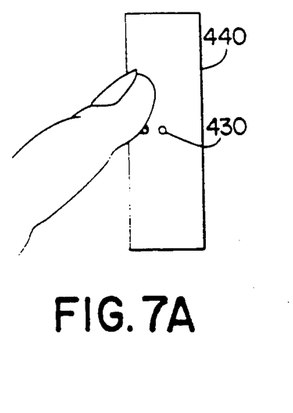
FIG. 7a is a rear view of an individual folded strip of FIG. 6.
Figure 7B:
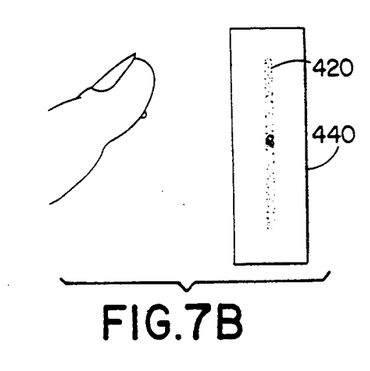
FIG. 7b is a cut away view of the inner folded strip as in FIG. 6.
Figure 7C:
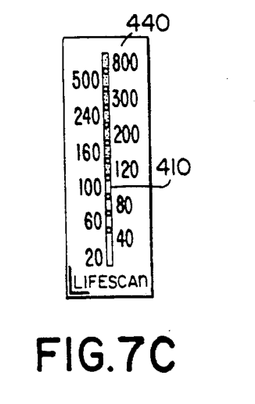
FIG. 7c is a front view of a reacted folded strip as in FIG. 6.

A blood sample is then applied to the hole 430 on the back of the strip 440, as in FIG. 7a. This sample migrates in both directions from the hole 430 in the capillary gap created in the strip 440, as in FIG. 7b, formed from slit 420, the coated membrane, and lower layer 425. The treated membrane first separates out red cells. Glucose in the remaining fluid reacts with enzymes to produce hydrogen peroxide, which in the presence of peroxidase, serves to decolorize (or colorizes) the indicator. This decolorization (or creation of color) occurs in the regions where the inhibitor and/or indicator concentrations are less than or equal to the proportional amount of glucose in the clear component fluid, which in turn parallels that on the whole blood sample. This results in a visual effect of colorized segments. Here, the segments disappear up to a given segment, which may be measured between about 40 mg/dl and 400 mg/dl in about 20 mg/dl increments. The last segment to change color is directly related to the glucose concentration on a numerical scale. FIG. 7c illustrates the appearance of a reacted strip 440 as seen through slit 410.

This visual test strip 440 therefore is able to be used without color matching, wiping, blotting, or precise timing. Also, there is a reaction, either that of subtration from colored to colorless, or the reverse. The reaction increases ease of usage, especially among the color-blind, who no longer need to perform a degree of color comparison.

Also, the membrane and reagents used produce a very unexpectedly rapid rate of reaction, less than about 30 seconds, more usually about 10 seconds.

Of course, two factors must be present. First, the reagent strip must have a matrix or matrices of the above specified thicknesses in order to appropriately separate the blood and create a large enough barrier to maintain the originally clear surface on the opposite or visual comparison side of the pad. Second, the varying color change must suitably reflect analyte concentration levels to the human eye or any other measuring device.

EXAMPLES

Example 1

A 1.5 inch by 10 inch strip of 0.45 micron hydrophillic anisotropic polysulfone membrane is dipped in a solution containing: 0.08% disodium EDTA; 17 mg/ml low viscosity Polypep TM; 0.2 M Aconitic acid buffer pH 5.5; 0.75% hydrolized Gantrez TM; 0.75 mg/ml bromopyrogallol red; 8.5 mg/ml glucose oxidase; and 1.5 mg/ml horseradish peroxidase. The excess solution is wiped off and the strip is dried in a 56° C. convection oven for ten minutes. At this point a distinct color difference is observed on the membrane, namely that the "skin" side is significantly darker than the "open" side. Thus, the strip is appropriately produced in accord with the invention, and is ready for application of whole blood sample. Sample is observable to capably determine blood glucose concentration levels useful for human measurement.

Example 2

A 1.5 inch by 10 inch strip of 0.2 micron hydrophobic anisotropic polysulfone membrane is dipped in a solution containing: 0.08% disodium EDTA; 30 mg/ml Bovine Serum Albumin, Fraction V; 3% polyethylene glycol 600; 0.2 M Aconitic acid buffer pH 5.5; 0.5% Polyquart TM; 0.5 mg/ml bromopyrogallol red; 10 mg/ml glucose oxidase; 4 mg/ml horseradish peroxidase; and 25% acetonitrile. The excess solution is wiped off and the strip is dried in a 56° C. convection oven.

After the membrane coated in the above examples is dry, inhibitor can be applied to it in a variety of possible designs by printing or other coating means. When the membrane is again dry it can be assembled into the appropriate test format. Again the test format is useful for determining human blood glucose concentration measurements.

Example 3

A 1.5 inch by 10 inch strip of 0.2 micron hydrophobic anisotropic polysulfone membrane is dipped in a solution containing: 0.08% disodium EDTA; 30 mg/ml Bovine Serum Albumin, Fraction V; 3% polyproplene glycol 400; 0.2 M Aconitic acid buffer pH 5.5; 0.5% Polyquart TM; 0.5 mg/ml bromopyrogallol red; 10 mg/ml glucose oxidase; 4 mg/ml horseradish peroxidase; and 25% ethanol. The excess solution is wiped off and the strip is dried in a 56° C. convection oven.

After the membrane coated in the above examples is dry, inhibitor can be applied to it in a variety of possible designs by printing or other coating means. When the membrane is again dry it can be assembled into the appropriate test format. Again the test format is useful for determining human blood glucose concentration measurements. Importantly, however, this arrangement proved much more stable than those described in Examples 1 and 2. In this way, this format describes a system with more versatile characteristics and, perhaps, longer shelf life.

It is well recognized that once the separating agent has separated the red blood cells or hemoglobin from the whole blood sample, one is capable of performing any desired test for analyte present in such separated constituent. Specifically, with appropriate reagents, one can measure cholesterol or alcohol levels in whole blood. Such is an intended use of the present device in conjunction with the appropriate known reagents embedded within the matrix.

It is therefore intended that the previous examples not limit the scope of the present invention which is to be determined from the following claims and their equivalents.

What is claimed is:

1. A reagent strip comprising:
   a porous matrix having sample side and a test side, said matrix uniformly impregnated with a separation coating and a testing reagent;
   an upper support member upon which the matrix is mounted, having a slit which extend through the upper support member and permits visual observation of the test side;
   a lower support member having a hole therethrough, said lower support member and said upper support member substantially surrounding the matrix;
   said lower support member and said matrix defining a capillary gap therebetween which communicates with the hole and with a portion of the sample side opposite the slit;
   said matrix having a pore size distribution suited to accept a whole blood sample suspected of containing glucose as an analyte applied onto said sample side via the hole and to pass said sample toward said test side by capillary actions;
   said separation coating capable of separating from said whole blood a substantially clear component fluid containing said glucose by selectively retarding the passage of red blood cells through the matrix;
   said testing reagent comprising an enzyme, a dye indicator, and a dye inhibitor capable of reacting with said glucose in said clear component fluid to vary coloration of the test side of said matrix, dependent upon the concentration level of the glucose in said fluid;
   wherein said separation coating is selected from the group consisting of polyvinyl sulfonic acid, polyethylene glycol, polystyrene sulfonic acid, hydroxypropyl cellulose, polyproplene glycol, polyvinyl pyrrolidone and polyacrylic acid; and said indicator and said inhibitor are present together on said matrix in bands, such that each band corresponds to one of two or more predetermined glucose concentrations and the presence of glucose concentrations in said whole blood sample which are equal to or greater than said predetermined concentrations may be detected by inspecting each band on the test side though said slit for variations in coloration.

2. The reagent strip of claim 1 wherein said testing reagent comprises glucose oxidase, horseradish peroxidase and an indicator selected from the group consisting of alizarin cyanin green, bromopyrolgallol red, anazolene sodium, pyrogallol- sulphophthalein, 2,2' azino-di-[3]ethylbenzthiazoline sulfonate.

3. The reagent strip of claim 1 further comprising a buffer selected from the group consisting of aconitic acid, malic acid, citric acid, and fumaric acid.

4. The reagent strip of claim 1 further comprising ethylene diamine tetraacetic acid as a chelator and an inhibitor selected from the group consisting of propyl gallate, ascorbic acid, gallic acid, isoascorbic acid, 3,4 dihydroxy cinnamic acid, 3,4 dihydroxybenzaldehyde, and 5,6-diaminouracil.

5. A reagent strip comprising:

a porous matrix having a sample side and a test side, said matrix uniformly impregnated with a separation coating and a testing reagent;

an upper support member upon which the matrix is mounted, having a slit which extends through the upper support member and permits visual observation of the test side;

a lower support member having a hole therethrough, said lower support member and said upper support member substantially surrounding the matrix;

said lower support member and said matrix defining a capillary gap therebetween which communicates with the hole and with a portion of the sample said opposite the slit;

said matrix, when applied on said sample side with a sample of whole blood suspected of containing glucose as an analyte, capable of accepting said whole blood sample through the hole so as to pass the sample toward said test said by capillary action;

said separation coating capable of separating from said whole blood a substantially clear component fluid containing said analyte by selectively retarding the passage of red blood cells through the matrix;

said testing reagent containing an indicator selected from the group consisting of alizarin cyanin green, bromopyrogallol red, anazolene sodium, pyrogallol red, and 2,2' azino-di-[3] ethylbenzthiazoline sulfonate, and capable of reacting with said analyte in said clear component fluid to vary coloration of the test side of said matrix, dependent upon the concentration level of the analyte in said fluid;

wherein said separation coating is selected from the group consisting of polyvinyl sulfonic acid, polyethylene glycol, polystyrene sulfonic acid, hydroxypropyl cellulose, polypropylene glycol, polyvinyl pyrrolidone and polyacrylic acid;

said matrix also has had coated to ti: enzymes comprising glucose oxidase and horseradish peroxidase which react with said analyte; a buffer selected from the group consisting of 2-(N-morpholine)-ethane acid, fumaric acid, malic acid, citric acid, and aconitic acid; and an inhibitor selected from the group consisting of 2,3,4-trihydroxybenzoic acid, propyl gallate, ascorbic acid, isoascorbic acid, 3,4 dihydroxy cinnamic acid, 3,4 dihydroxy benzaldehyde, gallic acid, and 5,6 diaminouracil; and said indicator and said inhibitor are present together on said matrix in bands, such that each band corresponds to one of two or more predetermined glucose concentrations and the presence of glucose concentrations in said whole blood sample which are equal to or grater than said predetermined concentrations may be detected by inspecting each band on the test side through said slit for variations in coloration.

6. The reagent strip of claim 5 wherein said bands are in 30 mg/dl intervals between 40 mg/dl and 400 mg/dl.

7. The reagent strip of claim 5 wherein said capillary gap is formed along one side of said matrix by a sheet of relatively impermeable material which has an elongated slit therein.

* * * * *

UNITED STATES PATENT AND TRADEMARK OFFICE
CERTIFICATE OF CORRECTION

PATENT NO. : 5,306,623

DATED : April 26, 1994

INVENTOR(S) : Ernest J. Kiser et al.

It is certified that error appears in the above-identified patent and that said Letters Patent is hereby corrected as shown below:

Column 14, Line 39 "extend" should be "extends"

Column 15, Line 17 after "sulphophthalein," insert "and"

Column 16, Line 36 "grater" should be "greater"

Column 16, Line 41 "in 30" should be "in 20"

Signed and Sealed this

Twentieth Day of June, 1995

BRUCE LEHMAN

*Attest:*

*Attesting Officer*      *Commissioner of Patents and Trademarks*